(12) United States Patent
Bai et al.

(10) Patent No.: US 10,130,940 B2
(45) Date of Patent: Nov. 20, 2018

(54) HYDROGENATION CATALYST, ITS METHOD OF PREPARATION AND USE

(71) Applicant: ExxonMobil Chemical Patents Inc., Baytown, TX (US)

(72) Inventors: Chuansheng Bai, Phillipsburg, NJ (US); Jean W. L. Beeckman, Columbia, MD (US); Adrienne J. Thornburg, Columbus, OH (US); Natalie A. Fassbender, Nazareth, PA (US); Sabato Miseo, Pittstown, NJ (US); Stuart L. Soled, Pittstown, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 31 days.

(21) Appl. No.: 15/910,403

(22) Filed: Mar. 2, 2018

(65) Prior Publication Data
US 2018/0185824 A1    Jul. 5, 2018

Related U.S. Application Data

(62) Division of application No. 14/916,727, filed as application No. PCT/US2014/053675 on Sep. 2, 2014, now Pat. No. 9,943,829.

(60) Provisional application No. 61/892,561, filed on Oct. 18, 2013.

(30) Foreign Application Priority Data

Dec. 17, 2013  (EP) ..................................... 13197587

(51) Int. Cl.
| | | |
|---|---|---|
| C07C 69/74 | (2006.01) |
| B01J 23/00 | (2006.01) |
| B01J 23/46 | (2006.01) |
| C07C 67/303 | (2006.01) |
| C07C 29/149 | (2006.01) |
| B01J 37/02 | (2006.01) |
| B01J 35/10 | (2006.01) |
| B01J 35/00 | (2006.01) |
| B01J 31/12 | (2006.01) |
| B01J 23/44 | (2006.01) |
| B01J 23/42 | (2006.01) |
| B01J 37/18 | (2006.01) |
| B01J 37/10 | (2006.01) |
| B01J 37/08 | (2006.01) |
| B01J 27/24 | (2006.01) |
| B01J 21/08 | (2006.01) |

(52) U.S. Cl.
CPC ............ *B01J 23/462* (2013.01); *B01J 23/42* (2013.01); *B01J 23/44* (2013.01); *B01J 23/464* (2013.01); *B01J 31/123* (2013.01); *B01J 35/002* (2013.01); *B01J 35/1014* (2013.01); *B01J 35/1019* (2013.01); *B01J 35/1061* (2013.01); *B01J 37/0203* (2013.01); *B01J 37/0207* (2013.01); *B01J 37/0209* (2013.01); *B01J 37/0242* (2013.01); *B01J 37/0244* (2013.01); *B01J 37/08* (2013.01); *B01J 37/10* (2013.01); *B01J 37/18* (2013.01); *C07C 29/149* (2013.01); *C07C 67/303* (2013.01); *B01J 21/08* (2013.01); *B01J 27/24* (2013.01); *B01J 2531/821* (2013.01); *B01J 2540/62* (2013.01)

(58) Field of Classification Search
None
See application file for complete search history.

(56) References Cited

U.S. PATENT DOCUMENTS

| | | |
|---|---|---|
| 4,628,129 A | 12/1986 | Bartley |
| 5,334,779 A | 8/1994 | Kuo |
| 5,936,126 A | 8/1999 | Rühl et al. |
| 2002/0019559 A1 | 2/2002 | Brunner et al. |
| 2004/0087672 A1 | 5/2004 | Yao et al. |
| 2010/0133148 A1 | 6/2010 | Timmler et al. |
| 2011/0082311 A1 | 4/2011 | Soled et al. |
| 2012/0071700 A1 | 3/2012 | Huang et al. |
| 2012/0184430 A1 | 7/2012 | Lee et al. |
| 2012/0296111 A1 | 11/2012 | Königsmann et al. |

FOREIGN PATENT DOCUMENTS

| | | |
|---|---|---|
| WO | 2004/045767 A | 6/2004 |
| WO | 2004/046076 A | 6/2004 |
| WO | 2004/046078 A | 6/2004 |

OTHER PUBLICATIONS

Quintanilla, A., et al., "Tuning the support adsorption properties of Pd/SiO2 by silylation to improve the selective hydrogenation of aromatic ketones", Journal of Catalysis, vol. 257, No. 1, pp. 55-63, (2008).

*Primary Examiner* — Ana Z Muresan
(74) *Attorney, Agent, or Firm* — Darryl M. Tyus

(57) ABSTRACT

A method of preparing a hydrogenation catalyst, for example, a phthalate hydrogenation catalyst, comprising contacting a silica support having a median pore size of at least about 10 nm with a silylating agent to form an at least partially coated silica support, calcining said coated silica support to form a treated silica support, and depositing a noble metal, preferably ruthenium, on the treated silica support, and optionally contacting the treated silica support with an optional chelating agent to form the hydrogenation catalyst; a hydrogenation catalyst prepared by that method; and a method of hydrogenating unsaturated hydrocarbons, such as phthalates, in which an unsaturated hydrocarbon is contacted with hydrogen gas in the presence of the hydrogenation catalyst of the invention.

15 Claims, No Drawings

HYDROGENATION CATALYST, ITS METHOD OF PREPARATION AND USE

CROSS REFERENCE TO RELATED APPLICATIONS

This application is a divisional application of U.S. application Ser. No. 14/916,727, filed Mar. 4, 2016, now allowed, which is a National Stage Application of International Application No. PCT/US2014/053675 filed Sep. 2, 2014, which claims priorities to U.S. Provisional Application Ser. No. 61/892,561, filed Oct. 18, 2013, and European Application No. 13197587.2, filed Dec. 17, 2013, the disclosures of each are fully incorporated herein by reference in their entireties.

FIELD OF THE INVENTION

The present invention relates to hydrogenation catalysts, in particular to methods for the preparation of noble metal catalysts, such as ruthenium (Ru) catalysts, for use in the hydrogenation of phthalates.

BACKGROUND

Plasticizers are incorporated into resins to increase their flexibility, workability, and dispensability. Phthalates, especially, the high molecular weight phthalates (HMWP), are used as plasticizers in PVC. Alternatives to phthalates are desirable due to environmental, legislative and regulatory concerns. In particular, the uses of phthalates as plasticizers are under severe pressure. Hydrogenation of phthalates produces 1,2-cyclohexyl dicarboxylates, hereinafter also referred to as cyclohexanoates, which can be also used as plasticizers.

Previous research showed that catalysts consisting of Ru supported on alumina ($Al_2O_3$) with low surface areas are active for the hydrogenation of phthalate to cyclohexanoates. U.S. Pat. No. 5,936,126 (BASF) discloses the hydrogenation of phthalates to cyclohexyl dicarboxylates using catalysts consisting of Ru supported on low surface area alumina at 80 to 120° C. and under 10-20 MPa (100-200 atmospheres) pressure. US 2002/0019559 (BASF) discloses a catalyst for hydrogenation of phthalates comprising ruthenium deposited on an alumina support material that comprises macropores of greater than 50 nm in diameter.

It has also recently been discovered that materials consisting of Ru supported on a silica ($SiO_2$) support with "remnant structure" produced by deposition of an organic ruthenium compound on a silica support to form an organic ruthenium complex on or in the support, followed by decomposition of the complex, have much higher activities and stabilities in the phthalate hydrogenation than reported $Ru/Al_2O_3$ catalysts. WO 2004/046076, WO 2004/045767 and WO 2004/046078 (ExxonMobil) disclose catalysts of Ru on silica supports prepared with the remnant structures. US 2012/0296111 (BASF) discloses an eggshell catalyst for hydrogenating carbocyclic aromatic compounds, such as phthalates, comprising a noble metal, such as ruthenium, deposited on a silica support material in which at least 90% of the pores present have a pore diameter of 6 to 12 nm. The catalysts may be prepared by depositing ruthenium acetate on the silica support and then reducing.

Large pore extruded silica is a commercial catalyst support. US 2010/0133148 (ExxonMobil) discloses a hydrodesulfurization catalyst comprising cobalt and molybdenum salts impregnated on large pore silica supports. The catalyst is prepared by impregnating the silica support with a solution containing the metal ions, an organic additive, which is an alcohol or aminoalcohol, an organic acid and an inorganic acid. US 2012/0184430 (Samsung) discloses the synthesis of a metal oxide support material, such as mesoporous silica, that has surface hydroxyl groups, including hydroxyl groups within its pores, and the preparation of a carbon dioxide reforming catalyst comprising a metal deposited onto that support material. However, the use of large pore silica as an effective support for ruthenium in a phthalate hydrogenation catalyst has not previously been achieved.

It has also been found that large pore silica support can facilitate the mass transfer of large molecules of phthalate during catalytic reactions, which can be beneficial to the catalyst activity for phthalate hydrogenation to cyclohexanoates. However, in order to have large pores and high crush strength, the silica support is steam-treated at high temperature. During the high temperature steam-treatments, improved extrudate crush strength and large porosity are accompanied by decreases in hydroxyl group concentration and surface area of the steamed silica support. As a consequence, known strong and large pore silica supports usually have low surface areas and low concentration of hydroxyl groups due to high temperature steaming. Si—OH hydroxyl groups are required for complexion to noble metals, such as ruthenium. Therefore, commercially available large pore silica are not particularly suitable for use as ruthenium supports for phthalate hydrogenation catalysts.

There remains a need for metal oxide-supported noble metal catalysts which are highly active in phthalate hydrogenation. In particular, there remains a need for a metal oxide support that can both facilitate the mass transfer of large molecules of phthalate during catalytic reactions and which has a high concentration of hydroxyl (Si—OH) groups for complexion to noble metals, such as ruthenium.

SUMMARY OF THE INVENTION

In a first aspect, the invention provides a method for the synthesis of a silica-supported noble metal catalyst, in particular a silica-supported ruthenium catalyst, in which a noble metal, preferably ruthenium, and optionally a chelating agent, is deposited onto a silica support that has been treated to add a fresh layer of silica onto the surface of the silica support material. Advantageously, the treatment of the silica support increases the concentration of hydroxyl (Si—OH) groups on the surface. In one embodiment, the invention provides a method for the preparation of a silica-supported noble metal (e.g., ruthenium) hydrogenation catalyst comprising the steps of: (a) contacting a silica support with a silylating agent to coat at least a part of the silica support to produce a coated silica support; (b) calcining the coated silica support obtained in step (a) to produce a treated silica support; and (c) depositing a noble metal (e.g., ruthenium) on the treated silica support obtained in step (b), such as by contacting the treated silica support obtained in step (b) with a solution comprising said noble metal (e.g., ruthenium) and an optional chelating agent, for instance triethanolamine (TEA), to produce a noble metal-containing silica support. The noble metal-containing silica support obtained in step (c) may be used as such as hydrogenation catalyst or it may be subjected to further processing steps before being used as a catalyst. The silica support used in step (a) is preferably a large pore silica support, for example, produced by steam-treating. The silica may, for example, have a median pore size of at least 10 nm, especially at least 20 nm. Additionally or alternatively, the silica support may have a high crush strength, for example, a crush strength of at least 800 g/mm, in particular at least 1000 g/mm. The method may further comprise the step of steam-treating a silica to produce the silica support used in step (a). The silylating agent is preferably a polysiloxane. In a preferred embodiment, the coated silica support of step (a) comprises at least a partial coating of a silylating agent on a large pore silica support. The method of the present invention optionally further comprises drying the coated silica support prepared in step (a), prior to calcining in step (b). The method of the first aspect of the invention optionally further comprises the step of drying and/or (d) calcining the noble metal-containing silica support obtained in step (c). The method optionally further comprises the step (e) of activating the catalyst for instance by contacting the noble metal-containing silica support obtained in step (c) or (d) with hydrogen gas to form an activated catalyst.

In a second aspect, the invention provides a silica-supported noble metal catalyst comprising a noble metal, preferably ruthenium, dispersed on a large pore silica support coated with a fresh silica layer. In particular, the invention provides a silica-supported noble metal hydrogenation catalyst comprising a noble metal, preferably ruthenium, dispersed on a silica support, wherein the median pore size of the catalyst is at least about 10 nm, especially at least 20 nm. Advantageously, the catalyst of the second aspect of the present invention has a hydrogen to noble metal chemisorption ratio of at least about 0.50, especially at least 0.60. Advantageously, the catalyst of the second aspect of the invention has a crush strength of at least 800 g/mm, in particular at least 1000 g/mm. The silica-supported noble metal, preferably ruthenium, catalyst of the second aspect of the invention may, for example, be prepared by the method of the first aspect of the invention. The hydrogenation catalysts of the invention are suitable for the catalysis of hydrogenation processes, for example, processes in which unsaturated hydrocarbons, such as aromatic compounds, are hydrogenated using hydrogen gas, especially for use in phthalate hydrogenation processes.

In a third aspect, the invention provides a method of hydrogenating phthalates comprising the step of contacting a phthalate with a catalyst of the second aspect of the invention or a catalyst obtainable or obtained by the method of the first aspect of the invention, for example, in the presence of hydrogen gas.

In a fourth aspect, the invention provides a method of increasing the concentration of hydroxyl (Si—OH) groups on the surface of a silica catalyst support material, for example, a large pore silica support, such as a silica support having a median pore size of at least 10 nm, especially at least 20 nm, comprising the step of treating the silica support with a silylating agent. For example, the invention provides a method of increasing, for example, repopulating, the hydroxyl group concentration of a silica support following steam treatment, the method comprising the step of treating the silica support by contacting with a silylating agent and then calcining.

In a fifth aspect, the invention provides a silica support having a median pore size of at least 10 nm, especially at least 15 nm, and a hydroxyl group concentration sufficient to provide a catalyst having hydrogen to noble metal chemisorption ratio of at least 0.5, especially at least 0.6, following deposition of the noble metal on the catalyst surface. Advantageously, the large pore silica support of the fifth aspect of the invention or prepared by the fourth aspect of the invention has a crush strength of at least 800 g/mm, for example, at least 1000 g/mm. The silica support of the fifth aspect of the invention may, for example, be prepared by increasing the hydroxyl (Si—OH) group concentration of a large pore silica support, such as a commercially available large pore silica support, or a silica support which has been steam-treated, in accordance with the method of the fourth aspect of the invention.

It has been found that treating silica supports with a silylating agent to form a silica coating or silica layer at the surface of the silica support improves the dispersion of noble metals, for instance ruthenium, onto the silica support. Without wishing to be bound by any theory, it is believed that treating a silica support that has been modified by high temperature steaming with a silylating agent, repopulates the hydroxyl groups on silica surface increasing the concentration of hydroxyl groups for noble metal anchoring and restores the surface areas which were lost during the high temperature steaming. It has also been found that following coating of the silica supports with fresh layers of active silica, the properties of high crush strength and large porosity of a steam-treated silica support are preserved. Hydrogen chemisorption experiments have demonstrated that noble metal dispersion on a large pore silica support suitable for phthalate hydrogenation is greatly improved with treated silica supports of the invention. To form silica-supported noble metal hydrogenation catalysts of the invention, the noble metal is preferably dispersed on a treated silica support with a chelation aid. Suitable chelation aids include amino alcohols, such as triethanolamine (TEA). For instance, TEA and Ru ions form complexes of Ru-TEA, which are anchored to the silica surface via the interactions with hydroxyl groups of a silica support. The hydroxyl groups of the silica support are the anchoring points for noble metal dispersion.

DETAILED DESCRIPTION OF THE INVENTION

The noble metal present in the catalyst of the present invention is selected from the group consisting of ruthenium, rhodium, palladium, platinum, and mixtures thereof, preferably ruthenium, most preferably ruthenium as the sole active metal.

The silica support used in step (a) typically has the property of high crush strength as well as large pore sizes. Such silica support may be produced by high temperature steaming. Silica catalyst supports having those properties are commercially available. The silica support used in the present invention typically has a median pore size of at least about 10 nm, for example, at least about 15 nm, especially at least about 20 nm, such as at least about 25 nm. The silica support used in the present invention preferably has a median pore size of no more than about 300 nm, for example, no more than about 200 nm, especially no more than about 150 nm. For example, the silica support may have a median pore size of from about 10 to about 100 nm, such as from about 15 nm to about 80 nm. The median pore size may be determined by mercury porosimetry, for example, according to ASTM D4284-12. The pores may be approximately spherical or an irregular shape. The pore size is the largest dimension of the pore, which is also known in the art as to as the "pore diameter" or "pore axis". Typically the silica support has a crush strength of at least 800 g/mm, for example, at least 1000 g/mm, preferably at least 1200 g/mm. Crush strength is measured using the standard test method for single pellet crush strength of formed catalyst shapes set out in ASTM D4179-01. Suitable silica supports having the properties described above are described in U.S. Pat. No. 8,216,958 (ExxonMobil), the disclosure of which is incorporated herein by reference.

The silica support used in the method of the invention can have any suitable shape or form. Preferably, the silica support is in the form of tablets, pellets, extrudates, spheres, and the like and combinations thereof. The extrudates may be of any cross section, for example, circular to form cylinders or tubes as well as trilobe or quadrulobe to form prisms. The silica support is typically a silica extrudate or a silica bead, preferably a silica bead.

If the silica support particles used in the method of the first aspect of the present invention are in the form of silica beads, spheres, tablets or pellets, the particle size distribution of said silica support may be determined by dry sieve analysis according to ASTM C136-96a. Said particle size distribution may be characterized by its D10, D50 and D90 values where D50 corresponds to the size at which 50 wt % of the sample is smaller and 50 wt % of the sample is larger. In the present invention, D50 is used to characterize the silica support average particle size or average diameter. The width or span of the particle size distribution is calculated as (D90−D10)/D50. The particle size distribution of a population of particles used in the present invention is typically relatively narrow, for instance with a span equal to or lower than 2, preferably equal to or lower than 1.5, more preferably equal to or lower than 1, in particular equal to or lower than 0.5 such as about 0.2.

If the silica support particles used in the method of the first aspect of the present invention are the form of extrudates, i.e., in the form of elongated shapes having a substantially constant cross section which corresponds to the hole of the extrusion die, the silica support particles may be characterized by an average length, an average diameter and an average aspect ratio. According to the present invention, the length of an extrudate corresponds to the extruded length of said extrudates, the diameter of an extrudate corresponds to the outside diameter of said extrudate cross section, i.e., the diameter of the smallest circle circumscribing the cross section, and the aspect ratio of an extrudate corresponds to the ratio of its length on its diameter. Thus, for example, for a cylindrical extrudate, the diameter of the particle corresponds to the diameter of the disc cross section. For an extrudate having an elliptic cross section, the diameter of the particle is the major axis of the ellipse, i.e., the line segment that runs through the center and both foci, with ends at the widest points of the extruded elliptical cross section. For a symmetric quadrulobe extrudate, the diameter is the highest dimension of the quadrulobe section, i.e., the longest distance, in a straight line between two points on the quadrulobe cross section and its center. The diameter of an extrudate is substantially constant, as the cross section of the extrudate is dictated by the size of the hole in the extrusion die. The average length, average diameter, and average aspect ratio of the extrudate silica support particles of the present invention may be determined by optical scanner imaging using ALIAS Image Analysis System (Cascade Data System). The sample size is typically of 150 to 250 particles, without sample preparation per se. The average length and average diameter are the numerical averages (arithmetic means) of the measured individual lengths and diameters while the aspect ratio is the fraction of said average length on said average diameter. The average length of the extrudate silica support particles used in the method of the first aspect of the invention can vary widely and is not critical. In the present invention, the average length to diameter aspect ratio of said extrudate silica support particles is usually at least 1, most often higher than 1, typically at least about 2, in particular at least about 2.5, for example, at least about 3. Said average aspect ratio is usually at most about 10, typically at most about 8, for instance at most about 5.

The average diameter of the silica support particles used in the method of the first aspect of the invention, whether beads, spheres, tablets or pellets, extrudates or other forms, is generally in the range of from about 0.8 mm to about 10 millimeters (mm), preferably in the range of from about 1.0 mm to about 5 mm, and more preferably in the range of from about 1.2 mm to about 3 mm, such as from about 1.3 mm to about 2 mm. Preferably, the average diameter of the particles is no more than about 2.4 mm, for example no more than about 2.2 mm, especially no more than about 2.0 mm. In some embodiments, the silica support consists of particles having an average diameter of less than about 2.0 mm, for example, no more than about 1.8 mm, especially no more than about 1.7 mm. Typically, the particles have an average diameter of at least 0.7 mm. Preferably, the silica support consists of particles having an average diameter of from about 0.8 mm to about 2.2 mm, especially from about 1.0 mm to about 2.0 mm, for example, from about 1.2 mm to about 1.8 mm. The catalyst of the second aspect of the invention typically consists of particles of substantially the same size as the silica support listed above. For example, a catalyst of the second aspect of the invention based on silica support particles in the form of beads, spheres, tablets, pellets or extrudates, preferably consists of particles having an average diameter of from about 0.7 mm to about 2.4 mm, especially from about 0.8 mm to about 2.2 mm, for example, from about 1.0 mm to about 2.0 mm. The average diameter of the particles of support or catalyst may, for example, be measured by dry sieve analysis and/or optical scanner imaging as appropriate.

The silica support used in the method of the invention has advantageously been steam treated. The method of the first or third aspects of the invention optionally comprises the additional step of heating a silica, for example, a silica extrudate, in the presence of steam prior to step (a). The silica material is optionally heated to a temperature of at least 400° C., such as at least about 450° C., for example, a temperature in the range of from about 500° C. to about 800° C. in the presence of steam, for example, in an atmosphere comprising at least 5 wt % steam, especially at least 10 wt % steam. The step of steam treating a silica material advantageously increases the crush strength and/or the pore size of the silica and can therefore be used to prepare a silica support having a large pore size, e.g., a pore size of 10 nm or greater, especially 15 nm or greater, and a high crush strength, e.g., a crush strength of 800 g/mm or greater, especially 1000 g/mm or greater.

The silica support preferably has a silica content of at least 60 wt %, for example, at least 80 wt %. In addition to silica, the silica support may, for example, also comprise alumina however alumina is preferably a minor component. Accordingly, the silica support preferably comprises no more than 40 wt % alumina, for example, no more than 20 wt % alumina especially, no more than 10 wt % alumina.

The silica support used in the methods of the invention typically has a pore volume of at least about 0.2 ml/g, for example, at least about 0.5 ml/g, especially at least about 0.6 ml/g. The silica support typically has a pore volume of no more than about 3.0 ml/g, for example, no more than about 2.0 ml/g, especially no more than about 1.5 ml/g. For example, the silica support typically has a pore volume in the range of from about 0.2 ml/g to about 1.2 ml/g, such as from about 0.3 to about 1.0 ml/g or to about 0.8 ml/g. The pore volume may be determined by mercury porosimetry, for example, according to ASTM D4284-12. A silica support for use in preparing the treated silica support used in the present invention generally has a surface area, measured by the Brunauer, Emmett, Teller (BET) method, ASTM D1993, in the range of from about 20 m$^2$/g to about 400 m$^2$/g, preferably in the range of from about 40 m$^2$/g to about 300 m$^2$/g, and more preferably in the range of from about 50 m$^2$/g to about 200 m$^2$/g.

The silylating agent used in step (a) may be any suitable silicon-containing compound that effectively treats a silica support so as to repopulate the hydroxyl (Si—OH) groups on the surface of the silica support. Preferably, the silylating agent at least partially coats the silica support with silica, typically after calcination. Suitable silylating agents for use in treating the silica support according to the present invention include monomeric or oligomeric compounds having a plurality of siloxane groups attached to an organic core, in particular polysiloxanes and organosilicon compounds comprising multiple siloxane groups, such as polyalkyl siloxanes and poly(alkylaryl) siloxanes, most preferably poly(alkylaryl) siloxanes. The term "polysiloxane" as used herein refers to compounds having multiple siloxane (O—Si—O) functionality. Suitable polysiloxanes include polymerised siloxanes having an inorganic silicon-oxygen backbone (•••—Si—O—Si—O—Si—O-•••) with organic side groups attached to the silicon atoms, i.e., polymers with the chemical formula $[R_2SiO]_n$, where R is an organic group such as alkyl, in particular $C_{1-6}$ alkyl, especially $C_{1-4}$ alkyl, such as methyl or ethyl, and/or aryl, especially phenyl. Suitable examples of polysiloxanes are poly($C_{1-4}$ alkyl) siloxanes such as polydimethylsiloxane (PDMS); poly($C_{1-6}$ alkylphenyl) siloxanes, such as phenyl methyl polysiloxane (PPMS), full IUPAC name 1,1,5,5,5-hexamethyl-3-phenyl-3-((trimethylsilyl)oxy)trisiloxane; and silicone resins that comprise crosslinked matrices of branched and cage-like oligosiloxanes, for example, of the formula $R_nSiX_mO_y$, where R is a non-reactive substituent, usually alkyl or aryl, and X is a functional groups such as hydroxy. The treating agent may, for example, be an organosilicon compound selected from compounds having the following formulae: $SiR_yX_{4-y}$, $(R_wX_{3-w}Si)_2.Z$, $[SiR_mOX_{2-m}]_n$, $[SiR_mX_{2-m}]_n$, and combinations of any two or more thereof, wherein y=1 to 4; w=1 to 3; m=1 to 2; n>2, preferably >5, and more preferably in the range of from 10 to 5,000,000; R=alkyl, aryl, H, alkoxy, aryloxy, arylalkyl, alkylaryl; when y>=2 or w>=2 or m=2, R can be the same or different and is independently selected from the groups listed; X=halide; and Z=oxygen or imino or alkylimino or alkanoylimino. Suitable organosilicon compounds include those described in U.S. Pat. No. 7,030,053, the disclosure of which is incorporated herein by reference (see column 4, lines 15 to 44), for example, tetraethoxysilane.

Contacting step (a), wherein the silica support is contacted with the silylating agent, can be conducted by any manner or method that provides for an at least partially coated silica support that can be utilized in preparing a catalyst composition of the present invention. The contacting may, for example, comprise the step of impregnating and/or mixing the silylating agent, typically in solution, with the silica support. The solution may be an aqueous solution, an alcohol-containing solution, or a hydrocarbon solution of the treating agent. The treatment may, for example, involve contacting the silica support with a solution of the silylating agent in an organic solvent. The organic solvent may be an alkane solvent, for example, a $C_3$ to $C_{12}$ alkane or mixture of $C_3$ to $C_{12}$ alkanes, such as hexane, heptane, octane, nonane, decane, undecane, dodecane and mixtures thereof. A preferred impregnation technique is "incipient wetness impregnation" that includes essentially completely filling of the pores of the silica support with a solution of the silylating agent. The concentration of the silylating agent in the solution can range upwardly to the solubility limit of the silylating agent in the solvent. Generally, the concentration of the silylating agent in the solution can be in the range of from about 1 wt % to about 50 wt %, preferably in the range of from about 2 wt % to about 30 wt %, and more preferably in the range of from about 4 wt % to about 20 wt %. Said contacting step may be made at any suitable temperature and pressure, for instance at room temperature and atmospheric pressure.

Steps (a) and (b) result in an at least partially coated silica support, typically with one or more fresh silica layers, by the deposition of layers of polysiloxane compounds followed by a calcining step. Said treated silica support includes fresh silica on at least part of the surface of the silica support. Generally, a weight ratio of fresh silica coating to underlying silica support is in the range of from about 0.01:1 to about 0.30:1, preferably in the range of from about 0.03:1 to about 0.25:1, and more preferably in the range of from about 0.05:1 to about 0.20:1. Typically the additional silica added via the treatment steps (a) and (b) constitutes from about 8% to about 12% of the total weight of the treated silica support.

Generally, the amount of silylating agent deposited on the silica support in the methods of the present invention is in the range of from about 5 wt % to about 50 wt % based on the total weight of the support following contact with the silylating agent, preferably in the range of from about 10 wt % to about 40 wt %, and more preferably in the range of from about 12 wt % to about 35 wt %.

After contacting the silica support with a silylating agent in step (a) and before calcining step (b), the resulting coated silica support (containing a silylating agent) is optionally subjected to a drying step. The drying step may be carried out at a temperature in the range of from about 40° C. to about 180° C., preferably in the range of from about 5° C. to about 150° C., and more preferably in the range of from about 50° C. to about 130° C. The drying step may be performed under reduced pressure or under atmospheric pressure, in an inert atmosphere or in air, preferably in an inert atmosphere such as under nitrogen and under atmospheric pressure. The drying can also be promoted by passing a gas stream over or through the material to be dried, for example, air or nitrogen, preferably nitrogen. The drying time depends upon the desired degree of drying and the drying conditions and is preferably in the range of from 1 hour to 30 hours, preferably from 2 hours to 10 hours.

In addition to the optional drying step, the preparation of a treated silica support comprises a calcining step (b), conducted under calcining conditions, such as exposure to a high temperature, for example, in the range of from about 250° C. to about 1000° C., preferably in the range of from about 300° C. to about 900° C., and more preferably in the range of from about 400° C. to about 700° C. The calcining step is preferably conducted in the presence of oxygen, for example, in air or in an oxygen enriched environment comprising at least 30% by volume oxygen. The calcining step may also include heating in an inert environment, for example, under nitrogen, followed by calcination under a gas mixture comprising an inert gas and oxygen or air, such as a mixture of nitrogen and oxygen. During calcining, substantially all volatile matter (e.g., water and carbonaceous materials) is removed. The coated silica support is subjected to calcination to form a treated silica support prior to contacting with the noble metal in step (c). The step (a) of contacting a silica support with a silylating agent together with the calcination step (b) and optional intermediate drying step, are collectively referred to as a "treatment step" that produces a treated silica support.

Advantageously, the treatment of the silica support in steps (a) and (b) increases the concentration of hydroxyl groups on the silica support by at least 1 Si—OH group by per $nm^2$, for example, by at least 1.5 Si—OH group per $nm^2$. Silica Si—OH concentrations can, for example, be measured by reacting the active hydrogen of the hydroxyl groups of a known quantity of silica with a $C_2H_5MgBr$ ethyl magnesium bromide Grignard reagent to produce ethane $C_2H_6$. The volume of ethane evolved can be used to calculate active hydrogen of OH groups of the silica support. Alternatively, a calibration curve of standard silica materials with known OH concentrations can be made using Fourier Transform Infrared Spectroscopy (FTIR) and then the FTIR of a silica with an unknown OH concentration can be compared against the calibration curve. Advantageously, the treatment of the silica support increases the concentration of hydroxyl groups on the silica support such that the maximum hydrogen to noble metal chemisorption ratio (hereinafter also referred to as H/noble metal chemisorption ratio) that can be achieved following noble metal deposition is increased by at least 0.1 compared to the untreated silica support. As discussed in more detail below, the hydrogen to noble metal chemisorption ratio is an indication of the level of dispersion of the metal on the support and an indication of the availability of the metal atoms as catalytic sites. High hydrogen to noble metal chemisorption ratios are thus indicative of higher catalytic activity. Advantageously, the treatment of the silica support in steps (a) and (b) increases the concentration of hydroxyl groups on the silica support such that a hydrogen to noble metal chemisorption ratio in excess of 0.5 can be achieved after deposition of noble metal, preferably ruthenium, onto the silica support. Advantageously, the treatment step increases the surface area of the support as measured by the Brunauer, Emmett, Teller (BET) method, ASTM D1993. For example, the treated silica support produced in step (b) may have a BET surface area of at least about 10 $m^2/g$, preferably at least about 20 $m^2/g$, especially at least about 25 $m^2/g$ greater than the untreated silica support used in step (a). In some embodiments, the BET surface area is increased by at least about 30 $m^2/g$. Advantageously, the treated silica support has a surface area, measured by the BET method, of at least about 30 $m^2/g$, preferably at least about 40 $m^2/g$, and more preferably at least about 45 $m^2/g$. In some embodiments the treated silica support has a surface area, measured by BET method of at least about 50 $m^2/g$. Typically, the surface area as measured by the BET method is 300 $m^2/g$ or less, for example, 200 $m^2/g$ or less, such as 150 $m^2/g$ or less.

The step (c) of depositing a noble metal on the treated silica support to form a noble metal-containing silica support comprises contacting the treated silica support obtained in step (b) in any contacting manner with a noble metal, typically in the form of a precursor compound of said noble metal. Suitable precursor compounds are noble metal compounds which can be converted into metallic compounds. Examples of suitable contacting methods include, but are not limited to, impregnation, mixing, immersion, and the like. Generally, depositing a noble metal on a treated silica support according to a process of the present invention comprises an impregnation technique. Generally, the treated silica support is impregnated with a noble metal precursor dissolved in an aqueous solution such as deionized water, by immersing the treated silica support in the solution of the noble metal precursor, for example, by incipient wetness impregnation in which the pores of the treated silica support are filled with the solution. The treated silica support can also be sprayed with an impregnating solution containing a dissolved noble metal precursor component. The amount of noble metal precursor utilized in the method of the first aspect of the present invention is such as to provide a concentration of said noble metal on the treated silica support that is suitable to catalyze hydrogenation reactions, for example, the hydrogenation of phthalates into cyclohexanoates. Typically, the concentration of noble metal in a catalyst of the second aspect of the present invention is in the range of from about 0.1 wt % to about 5 wt % based on the total weight of the catalyst composition, preferably in the range of from about 0.1 wt % to about 2 wt %, and more preferably in the range of from about 0.2 wt % to about 1 wt %, especially from about 0.5 wt % to about 0.8 wt %, based on the total weight of the catalyst composition. Generally, the concentration of the noble metal precursor in the impregnating solution is in the range of from about 0.01 Molar (M) to about 1.0 M, preferably in the range of from about 0.01 M to about 0.20 M, and more preferably in the range of from about 0.02 M to about 0.10 M, especially from about 0.03 M to about 0.08 M. Examples of a suitable solvent of the impregnating solution include, but are not limited to, deionized water, an alcohol and combinations thereof.

The noble metal may be deposited on the surface of the treated silica support in any form, including salt forms, organo-metal compounds, metal oxides or complexes comprising noble metal atoms or ions. The noble metal is typically deposited onto the treated silica support as a salt, for example, in a suitable solvent, such as water or another polar protic solvent, such as $C_1$-$C_4$ alkanols, for instance methanol, ethanol, n-propanol or isopropanol. Suitable noble metal salts include nitrate, nitrosyl nitrate, halide (typically bromide, chloride or iodide) and acetate salts, in particular nitrosyl nitrate. Ruthenium nitrosyl nitrate salts are especially preferred. Alternatively, the noble metal may be deposited onto the treated silica catalyst support by contacting the treated silica support with noble metal oxide, for instance ruthenium oxide.

Advantageously, the noble metal is deposited on the silica support in the form of to a salt and in the presence of a chelating agent, for example, as a solution of a noble metal salt and a chelating agent, more preferably as a noble metal-chelating agent complex, for example, as a ruthenium-chelating agent complex. The formation of a noble metal-chelating complex typically inhibits undesired interactions among noble metal atoms, thus preventing noble metal particle agglomerations. The chelating agent advantageously acts as a dispersion aid.

The chelating agents for use in the methods of the invention include at least one and in particular from 1 to 6 nitrogen-containing functional groups selected from amine and imine functional groups (i.e., amino and/or imino groups), such as from 1 to 6 secondary or tertiary amine functional groups. Preferably the chelating agent also includes at least one carboxylic acid and/or hydroxyl functional group, preferably from 1 to 6 carboxylic acid and/or hydroxyl functional groups, more preferably from 2 to 6 carboxylic acid and/or hydroxyl functional groups. In a particular embodiment, the chelating agent has from 2 to 20 carbon atoms, for example, from 4 to 15 carbon atoms. Advantageously, the chelating agent comprises at least one carboxylic acid and/or hydroxyl functional group as well as at least one nitrogen-containing functional group selected from amine and imine functional groups (preferably amine functional group), and has from 2 to 20 carbon atoms. Especially suitable chelating agents are amino alcohols and/or amino carboxylic acids comprising 1 to 6 carboxylic acid and/or hydroxyl functional groups, preferably at least 2 carboxylic acid and/or hydroxyl functional groups, more preferably 2 to 6 carboxylic acid and/or hydroxyl functional groups and 1 to 6 nitrogen-containing functional groups selected from amine and imine groups, especially 1 to 6 amine groups, more particularly 1 to 6 secondary or tertiary amine groups, and 2 to 20 carbon atoms, preferably from 2 to 15 carbon atoms, for example, from 2 to 10 carbon atoms. Advantageously, the chelating agent comprises 1 to 6 hydroxyl functional groups, preferably 2 to 6 hydroxyl functional groups, and 1 to 6 amine or imine functional groups, especially 1 to 6 amine functional groups, preferably 1 to 6 secondary or tertiary amine groups, and 2 to 20 carbon atoms, in particular from 2 to 15 carbon atoms, especially 2 to 10 carbon atoms. Suitable chelating agent include those described in U.S. Pat. No. 3,761,428 (Institute Francais du Petrole) (see col. 1, lines 51 to 64) and those described in US 2010/0133148 (ExxonMobil) (see paragraphs [0038] to [0042]), the disclosure of both of which is incorporated herein by reference. Preferred chelating agents for use in the methods of the invention include $C_2$ to $C_{20}$ amino alcohols, including dialkanolamines, such as diethanolamine and dialkanoldiamines, and trialkanolamines, for instance triethanolamine (TEA). Other suitable chelating agents are amino carboxylic acids, including polyamino carboxylic acids, amino polycarboxylic acids, such as nitrilotriacetic acid (NTA), and polyamino polycarboxylic acids, such as ethylenediaminetetraacetic acid (EDTA), as well as polyamines, such as guanidine. Preferred chelating agents are TEA and EDTA, with TEA being especially preferred. Chelating agents comprising amine or imine functional groups have been found to form complexes with noble metal ions, such as Ru-TEA. Those complexes are advantageously anchored to the silica surface via the interactions with the hydroxyl groups (Si—OH) of the silica support. It has also been found that chelating agents comprising carboxylic acid or hydroxyl functional groups as well as at least one nitrogen-containing functional group selected from amine and imine groups form particularly strong interactions with the hydroxyl groups (Si—OH) of the silica support. Thus, chelating agents comprising amine and/or imine functional groups as well as carboxylic acid and/or hydroxyl functional groups have been found to be the most effective dispersion aids for noble metals. Typically, the noble metal is deposited on the silica support in the presence of an excess of chelating agent, for example, at least 5 molar equivalents of chelating agent, especially at least 10 molar equivalents of chelating agent, such as at least 15 molar equivalents of chelating agent.

After depositing the noble metal on the treated silica support, the resulting noble metal-containing silica support is optionally subjected to a washing and/or drying step. This washing step typically uses water. This drying step typically includes a temperature generally in the range of from about 20° C. to about 200° C., preferably in the range of from about 50° C. to about 175° C., and more preferably in the range of from about 75° C. to about 150° C. The drying step may be performed under reduced pressure or under atmospheric pressure, in an inert atmosphere or in air, most often in air and under atmospheric pressure. The drying can also be promoted by passing a gas stream over or through the material to be dried, for example, air or nitrogen. The drying time depends upon the desired degree of drying and the drying conditions and is preferably in the range of from 1 hour to 30 hours, preferably from 2 hours to 10 hours.

Further optionally, and alternatively or additionally to the drying step, the preparation of the silica-supported noble metal catalyst may comprise a calcination step (d) of the noble metal-containing silica support under a calcining condition, such as exposure to a high temperature, for example, in excess of about 200° C., preferably in excess of about 240° C., and more preferably in excess of about 260° C., for example, from about 200° C. to about 600° C., such as from about 240° C. to about 400° C. During calcining, substantially all volatile matter (e.g., water and carbonaceous materials) is removed. The optional calcination step (d) performed after contacting of the treated silica support with the noble metal is typically carried out at a lower temperature than the calcination step (b) performed after contacting the silylating agent and the silica support in step (a). For example, the optional calcination step (d), performed after deposition of the noble metal on the coated silica support, may be performed at a temperature of at least about 100° C., for example, at least about 200° C. less than the temperature of the calcination step (b) performed prior to the deposition of the noble metal on the silica support. The calcination step (d) is usually conducted in air.

Advantageously, the silica-supported noble metal catalyst produced by the process of the present invention is subjected to an optional activation step (e), in which the noble metal-containing silica support obtained in step (c) or (d) is contacted with hydrogen gas. Typically the activation step (e) takes place in an atmosphere comprising at least 60% by volume hydrogen, for example, at least 80% by volume hydrogen, especially at least 95% by volume hydrogen, for example, an atmosphere of essentially 100% hydrogen. Any gas present in addition to hydrogen is preferably an insert gas such as nitrogen. Typically the contacting with hydrogen gas takes place at an elevated temperature such as a temperature of at least about 200° C., for example, a temperature of at least about 300° C., especially a temperature of at least about 400° C. For example, the contacting with hydrogen gas takes place at a temperature of from about 300° C. to about 650° C., such as from about 400° C. to about 550° C. Typically the hydrogen pressure is slightly above ambient pressure, such as a pressure of from about 10 kPa gauge to about 100 kPa gauge, such as about 34 kPa gauge (5 psig), i.e., around 136 kPa absolute pressure. Typically, the silica-supported noble metal catalyst may be contacted with hydrogen gas for at least about 1 hour, such as for at least about 2 hours. Preferably, the silica-supported noble metal catalyst is contacted with hydrogen gas for no more than about 5 hours. Contacting of the silica-supported noble metal catalyst with hydrogen gas for about 2.5 hours has been found to be sufficient to fully activate the catalyst.

The activation step (e) may optionally be followed by a passivation step (f). Such a passivation step (f) can for instance be conducted by treating the catalyst briefly in an oxygen-containing gas, for example, air, but preferably with an inert gas mixture comprising from 1 to 10 volume percent of oxygen. It is also possible to use $CO_2$ or $CO_2/O_2$ mixtures. The passivation step may for instance be conducted at room temperature under atmospheric pressure for a few hours.

Advantageously, the catalyst of the second aspect of the invention and/or the catalyst produced by the method of the first aspect of the invention, has a hydrogen to noble metal chemisorption ratio, H/noble metal chemisorption ratio, preferably H/Ru chemisorption ratio, of at least about 0.50, especially at least about 0.60, preferably at least about 0.65. The H/noble metal chemisorption ratio is the molar ratio of hydrogen atoms absorbed on the catalyst for each noble metal atom and thus is a measure of the dispersion of the ruthenium on the catalyst. A H/noble metal chemisorption ratio of 1 would indicate that 100% of noble metal atoms are bound to a hydrogen atom after chemisorption of hydrogen and are thus fully dispersed, such that each noble metal atom is accessible for hydrogen binding. A H/noble metal chemisorption ratio of 0.5 indicates that only 50% of the noble metal atoms are able to bind to hydrogen, the remainder being inaccessible. Suitable conventional volumetric chemisorption techniques which can be employed to measure hydrogen chemisorption of the catalysts of the invention are discussed in Structure of Metallic Catalysts, J. R. Anderson, Academic Press, 1975, chapter 6. The hydrogen to noble metal chemisorption ratio can, for example, be calculated by reduction of a sample of silica-supported noble metal catalyst that contains a known quantity of noble metal with hydrogen and determining the quantity of hydrogen absorbed onto the catalyst, for example, by extrapolation of the isothermal profile to zero hydrogen pressure, after reduction of the sample at 200° C. in hydrogen for 30 minutes.

Advantageously, the catalyst produced in the method of the invention substantially retains the pore size of the silica support used in its preparation. Preferably, the catalyst of the second aspect of the invention and/or the catalyst produced in the method of the first aspect of the invention has a median pore size of at least about 10 nm, for example, at least about 15 nm, especially at least about 20 nm, such as at least about 25 nm. Advantageously, the catalyst produced in the method of the first aspect of the invention has a median pore size at least about 75%, for example, at least about 80%, especially at least about 85%, such as at least about 90% of that of the large pore silica support used in step (a).

The catalyst of the second aspect of the invention or the catalyst produced by the method of the first aspect of the invention is especially suitable as a hydrogenation catalyst, in particular for the hydrogenation of unsaturated hydrocarbons, especially phthalates, for instance dimethyl phthalate, di-2-propylheptyl phthalate, di-2-ethyl-hexyl phthalate, dioctyl phthalate, or diisononylphthalate.

In one embodiment of the second aspect of the invention, there is provided a silica-supported noble metal catalyst, preferably a silica-supported ruthenium catalyst, wherein the median pore size of the silica support is at least 10 nm, especially at least 15 nm; the catalyst has an H/Ru of at least 0.50, especially at least 0.60; and optionally the catalyst has a crush strength of at least 800 g/mm, for example, at least 1000 g/mm.

In one embodiment, the method of the first aspect of the invention is a method of producing a hydrogenation catalyst which comprises the steps of: providing a silica support having a median pore size of at least 10 nm, especially at least 20 nm, for example, by steam-treating a silica extrudate or other silica material; (a) contacting the silica support with a silylating agent to form a coated silica support; optionally drying the coated silica support; (b) calcining the coated silica support to form a treated silica support; (c) depositing ruthenium on the treated silica support of step (b) by contacting the treated silica support with a solution comprising ruthenium and a chelating agent wherein the chelating agent comprises at least one carboxylic acid or hydroxyl functional group as well as at least one nitrogen-containing functional group selected from amine and imine groups, to produce a ruthenium-containing silica support; optionally drying the ruthenium-containing silica support; optionally (d) calcining the ruthenium-containing silica support to form a silica-supported ruthenium catalyst; and optionally (e) activating the silica-supported ruthenium catalyst by contacting the silica-supported ruthenium catalyst with hydrogen gas.

In a further embodiment, the method of the first aspect of the invention is a method of producing a phthalate hydrogenation catalyst which comprises the steps of: providing a silica support having a median pore size of at least 10 nm, especially at least 20 nm, for example, by steam-treating a silica extrudate or other silica material; (a) contacting the silica support with a polysiloxane silylating agent to form a coated silica support; drying the coated silica support of step (a); (b) calcining the dried coated silica support to form a treated silica support; (c) depositing ruthenium on the treated silica support of step (b) by contacting the treated silica support with a solution comprising a ruthenium salt and a $C_{2-6}$ amino alcohol chelating agent to form a ruthenium-containing silica support; optionally drying the ruthenium-containing silica support; (d) calcining the ruthenium-containing silica support to form a silica-supported ruthenium catalyst; and optionally (e) activating the silica-supported ruthenium catalyst by contacting the silica-supported ruthenium catalyst with hydrogen gas. The catalyst may, for example, be made by impregnation of an aqueous solution of a ruthenium salt, advantageously ruthenium nitrosyl nitrate, in the presence of TEA onto a silica-coated large pore silica support. In the catalysts prepared by the method of the invention, the ruthenium may, for example, be dispersed in the form of an aqueous solution of ruthenium-TEA complex on a DOW 550 silica-coated large pore silica support.

EXAMPLES OF THE INVENTION

The following examples illustrate the present invention. Numerous modifications and variations are possible and it is to be understood that within the scope of the appended claims, the invention may be practiced otherwise than as specifically described herein.

Commercially available, large pore, RT-235, silica support in the form of cyclindrical extrudates having an average diameter of about 1.4 mm (1/18 inch), manufactured by Albemarle, was coated with phenyl methyl polysiloxane (DOW 550). The coated silica support was dried and calcined before its use as a treated silica support for the deposition of ruthenium by impregnation with a Ru-TEA solution. The RU-TEA impregnated silica samples were then dried and calcined in air. As a comparison, untreated RT-235 was also impregnated with a Ru-TEA solution, dried and calcined under the same conditions. The hydrogen chemisorptions of both resulting catalysts were compared.

Example 1—Preparation of Treated RT-235 Support

RT-235 silica extrudates were used as a starting material for the deposition of a $SiO_2$ coating of DOW 550 phenyl methyl polysiloxane silicone oil. In a fume hood, RT-235 silica extrudates were impregnated with a decane solution containing 7.8 wt % of DOW 550 silicone. The sample was placed in a drying oven then purged with nitrogen for 1 hour to remove air before drying. The sample was dried at about 70° C. (160° F.) overnight in nitrogen environment. After drying, the sample was placed in a box furnace for calcination. The calcining furnace was heated in the presence of $N_2$ from room temperature to about 540° C. (1000° F.) at 2.8° C./min (5° F./min). The furnace was held at about 540° C. (1000° F.) for 1 hour. The calcining atmosphere was then gradually switched from $N_2$ to a mixture gas containing 40% oxygen and 60% nitrogen in a period of 2 hours. The final calcining treatment was carried out in this 40% oxygen/60% nitrogen gas mixture at about 540° C. (1000° F.) for 6 hours. Typically, between about 8% and about 12% by weight of the treated silica support after air calcination was silica derived from the DOW 550 silicone oil coating. The treated RT-235 silica support is abbreviated as "DOW-550 coated RT-235".

Example 2—Characterization of Untreated and Treated Silica Supports

The untreated (RT-235) and treated (DOW-550 coated RT-235) silica supports were characterized by their BET surface area (ASTM D1993), median pore size (mercury porosimetry according to ASTM D4284-12), and pore volume (mercury porosimetry according to ASTM D4284-12). Said RT-235 and DOW 550 coated RT-235 silica supports were also compared to a conventional silica support sold by PQ Corporation, referred to as PQ $SiO_2$. The results are summarized in Table 1 below.

TABLE 1

| Silica supports | BET surface area ($m^2$/g) | Pore vol (ml/g) | Median pore diameter (nm) |
|---|---|---|---|
| PQ $SiO_2$ | 205 | 1.1 | 17.4 |
| RT-235 $SiO_2$ | 98 | 0.71 | 27.7 |
| DOW 550 coated RT-235 | 168 | 0.93 | 21.0 |

It can be seen from Table 1 that the treatment of RT-235 silica support with DOW 550 increased the BET surface area from 98 to 168 $m^2$/g. The DOW 550 silica coating also improved the pore volume of the RT-235 silica support from 0.71 ml/g to 0.93 ml/g.

Example 3—Ru/$SiO_2$ Catalyst Preparations by Ruthenium Impregnation and Calcination on Treated and Untreated RT-235 Supports Silica-supported ruthenium catalysts were prepared by incipient wetness impregnation. Untreated (RT-235) and treated (DOW-550 coated RT-235) silica supports were used as catalyst supports. The ruthenium precursor compound used in the catalyst preparation was ruthenium nitrosyl nitrate. The chelation aid added in the impregnation solution was triethanolamine (TEA). The mixture solution was prepared by adding appropriate amounts of TEA and ruthenium nitrosyl nitrate into distilled $H_2O$. The volume of the impregnation solution used was about 95% of the solution absorption capacity of the silica support. For example, 8.37 g of ruthenium nitrosyl nitrate solution containing 1.5 wt % Ru was added to 3.73 g of triethanolamine (TEA). 10 g of water was added to the mixture of Ru-TEA. The solution was stirred until it was clear. The total solution volume prepared was about 23.8 ml. The concentration of Ru in the solution was 0.05 M and TEA was 1.05 M. The molar ratio of TEA to Ru was 21. 25 g of silica supports was used in the catalyst preparation. After deposition of the ruthenium on the silica supports, the ruthenium-containing silica supports were dried in air at 100° C. for 12 hours and calcined in air at 275° C. for 1 hour with ramping rate of 5° C./min to produce a silica-supported ruthenium catalyst. The air flow rate inside the calciner was adjusted at 5 volume/volume catalyst/minute. The silica-supported ruthenium catalysts contained 0.5% Ru, with respect to the total weight of catalyst.

Example 4—Activation of the Ru/$SiO_2$ Catalysts by Reduction and Passivation

The reduction reactor was ramped from room temperature to 425° C. at 5° C./min rate. The silica-supported ruthenium samples prepared according to Example 3 were reduced at 425° C. for 2.5 hours with 100% hydrogen. The hydrogen pressure was 34 kPa gauge (5 psig) adjusted by backpressure regulator plus atmospheric pressure. The reduced catalysts were allowed to cool down to room temperature in a $H_2$ flow. When the temperature of the reactor reached room temperature, the $H_2$ flow was replaced with a mixture of 1% air balanced with $N_2$. The catalyst passivation was carried out at room temperature for 2 hours. The gas flow of 1% air/$N_2$ then was adjusted at 5 volume/volume catalyst/minute.

Example 5—Hydrogen Chemisorption and Elemental Analysis

A Micromeritics ASAP 2020 Chemi system was used to measure hydrogen chemisorption and calculate the Ru dispersion of the silica-supported ruthenium catalysts prepared according to Example 3. The silica-supported ruthenium hydrogenation catalyst samples were dried under helium at 200° C. for 30 minutes to remove any moisture. Sample reduction was carried out at 200° C. in hydrogen for 30 minutes. The ramping rate was controlled at 5° C./min. After reduction, the sample chamber was evacuated at 200° C. for 1 hour, then the reactor was cooled down to room temperature while the system was still under vacuum. The hydrogen isothermal was measured at room temperature. The H/Ru chemisorption ratio was calculated by extrapolation of the isothermal profile to zero hydrogen pressure.

The residual carbon and nitrogen contents of the silica-supported ruthenium catalysts of Example 3 were determined by chemiluminescence. The ruthenium and sodium contents of the catalysts were determined by X-ray fluorescence (XRF).

The results of the hydrogen chemisorption and elemental analysis are summarized in Table 2 below.

TABLE 2

| Catalyst supports | C and N (%) | Ru and Na (%) | H/Ru chemisorption ratio |
|---|---|---|---|
| RT-235 | C: 2.8<br>N: 1.0 | Ru: 0.53<br>Na: 0.19 | 0.39 |
| DOW 550 coated RT-235 | C: 2.9<br>N: 1.1 | Ru: 0.48<br>Na: 0.22 | 0.70 |

The results of Table 2 show residual carbon and nitrogen contents of respectively 2.8-2.9% and 1.0-1.1% for both untreated (RT-235) and treated (DOW 550 coated RT-235) supported catalysts, even after calcination at 275° C. in air for 1 hour according to the procedure of Example 3. Said carbon and nitrogen residue contents indicate the formation of organic remnants after partial decomposition of Ru-TEA complexes during said calcination step.

The results of Table 2 also show that the ruthenium dispersion on the treated silica support (DOW 550 coated RT-235) was greatly increased compared to the untreated RT-235 silica support, with a H/Ru chemisorption ratio of 0.70 compared to 0.39. The hydroxyl groups of the silica support are the anchoring points for the ruthenium. Without being bound by any theory, it is believed that the higher Ru dispersion on the silica surface, as shown by the higher H/Ru chemisorption ratio, results from a higher concentration of hydroxyl groups on the treated silica support, brought by the DOW 550 silica coating said higher Ru dispersion will thus generate more active sites for phthalate hydrogenation.

The present invention has been described and illustrated by reference to particular embodiments. Those of ordinary skill in the art will appreciate that the invention lends itself to variations not necessarily illustrated herein. For this reason, then, reference should be made solely to the appended claims for purposes of determining the true scope of the present invention.

The invention claimed is:

1. A method for the preparation of a silica-supported noble metal hydrogenation catalyst comprising the steps of:
   (a) providing a silica support having a median pore size of at least about 10 nm;
   (b) steam treating said silica support to increase the hydroxyl concentration on the surface of said silica support after streaming to produce a steamed silica support;
   (c) contacting said streamed silica support with a silylating agent to coat at least part of said streamed silica support to produce a coated silica support;
   (d) calcining said coated silica support obtained in step (c) to produce a treated and coated silica support; and
   (e) dispersing a noble metal by a chelating agent on said treated and coated silica support obtained in step (d) to produce said silica-supported noble metal hydrogenation catalyst having a median pore size of at least 10 nm and no more than 300 nm.

2. The method of claim 1, wherein said noble metal is selected from the group consisting of ruthenium, rhodium, palladium, platinum, and mixtures thereof.

3. The method of claim 2, wherein said noble metal is ruthenium.

4. The method of claim 1, wherein said chelating agent has from 2 to 20 carbon atoms and comprising at least one carboxylic acid or hydroxyl functional group and at least one nitrogen-containing functional group, wherein said nitrogen-containing functional group is an amine or an imine.

5. The method of claim 1, wherein said chelating agent is triethanolamine.

6. The method of claim 1, wherein the method further comprises the step (f) of calcining said silica-supported noble metal hydrogenation catalyst produced in step (e) to produce a calcined, silica-supported noble metal hydrogenation catalyst.

7. The method of claim 1, wherein said silica support used in step (a) has a median pore size of at least about 20 nm.

8. The method of claim 1, wherein said silylating agent used in step (c) is a polysiloxane.

9. The method of claim 1, wherein said silylating agent used in step (c) is a poly(alkylaryl) siloxane.

10. The method of claim 1, wherein the surface area of said silica support, as measured by the BET method, is increased, after steps (b) thru (e), by at least about 20 $m^2/g$ compared to said surface area of said silica support used in step (a).

11. The method of claim 1, wherein said hydroxyl group concentration of the treated and coated silica support obtained in step (d) is increased by at least 1 Si—OH group per $nm^2$ as compared to that of the silica support used in step (a).

12. The method of claim 1, wherein said silica-supported noble metal hydrogenation catalyst has a hydrogen to noble metal chemisorption ratio of at least about 0.50.

13. The method of claim 1, wherein said silica support used in step (a) has a crush strength of at least 800 g/mm.

14. The method of claim 1, further comprising the step of activating said silica-supported noble metal hydrogenation catalyst produced in step (e) by contacting said catalyst with hydrogen gas.

15. The method of claim 6, further comprising the step of activating said calcined, silica-supported noble metal hydrogenation catalyst produced in step (f) by contacting said catalyst with hydrogen gas.

* * * * *